(12) United States Patent
Liu et al.

(10) Patent No.: US 10,201,694 B2
(45) Date of Patent: Feb. 12, 2019

(54) MEDICAL CATHETER CONTROL VALVE

(71) Applicants: Liang-Chuan Liu, New Taipei (TW);
Shih-Wei Li, New Taipei (TW)

(72) Inventors: Liang-Chuan Liu, New Taipei (TW);
Shih-Wei Li, New Taipei (TW)

( * ) Notice: Subject to any disclaimer, the term of this patent is extended or adjusted under 35 U.S.C. 154(b) by 20 days.

(21) Appl. No.: 15/461,903

(22) Filed: Mar. 17, 2017

(65) Prior Publication Data
US 2018/0264253 A1 Sep. 20, 2018

(51) Int. Cl.
*A61M 39/22* (2006.01)
*F16K 31/56* (2006.01)

(52) U.S. Cl.
CPC .............. *A61M 39/22* (2013.01); *F16K 31/56* (2013.01); *A61M 2039/226* (2013.01); *A61M 2205/0216* (2013.01)

(58) Field of Classification Search
CPC ............ A61M 39/22; A61M 2039/226; A61M 2205/0216; F16K 31/56
See application file for complete search history.

(56) References Cited

U.S. PATENT DOCUMENTS 6,923,184 B1 * 8/2005 Russo ............... A61M 16/0463
128/200.26

* cited by examiner

*Primary Examiner* — Imani Hayman
(74) *Attorney, Agent, or Firm* — Rosenberg, Klein & Lee (57) ABSTRACT

A medical catheter control valve includes a valve body defining a fluid channel and a single open-end hole extended across the fluid channel, and a click-on mechanism consisting of a plunger unit with a through hole and a spring member and mounted in the single open-end hole. When click the plunger unit, the plunger unit is shifted to keep the through hole in alignment with the fluid channel for allowing a fluid to pass through the fluid channel. When push back the plunger unit, the through hole is deviated from the fluid channel and the fluid channel is blocked. Thus, the medical catheter control valve can be conveniently controlled with one single hand.

8 Claims, 10 Drawing Sheets

MEDICAL CATHETER CONTROL VALVE

BACKGROUND OF THE INVENTION

1. Field of the Invention

The present invention relates to medical catheter technology and more particularly, to a control valve used in a medical catheter for blood transfusion or liquid medicine injection, which can be conveniently operated with one single hand to close or open the fluid channel accurately.

2. Description of the Related Art

Catheters are widely used in medical facilities for blood transfusion and liquid medicine injection of the tube. In order to facilitate controlling the flowing of blood or liquid medicine when transfusing blood or injecting liquid medicine into the blood vessel of the patient or drawing the blood from the blood vessel of the patient, the catheter is equipped with a control device, i.e., control valve. In order to facilitate the operation in a control valve for this purpose should be operable with one single hand.

In order to facilitate the operation of the control valve of a medical catheter in the operating room, the control valve needs to be operable with one single hand.

Figure 9:
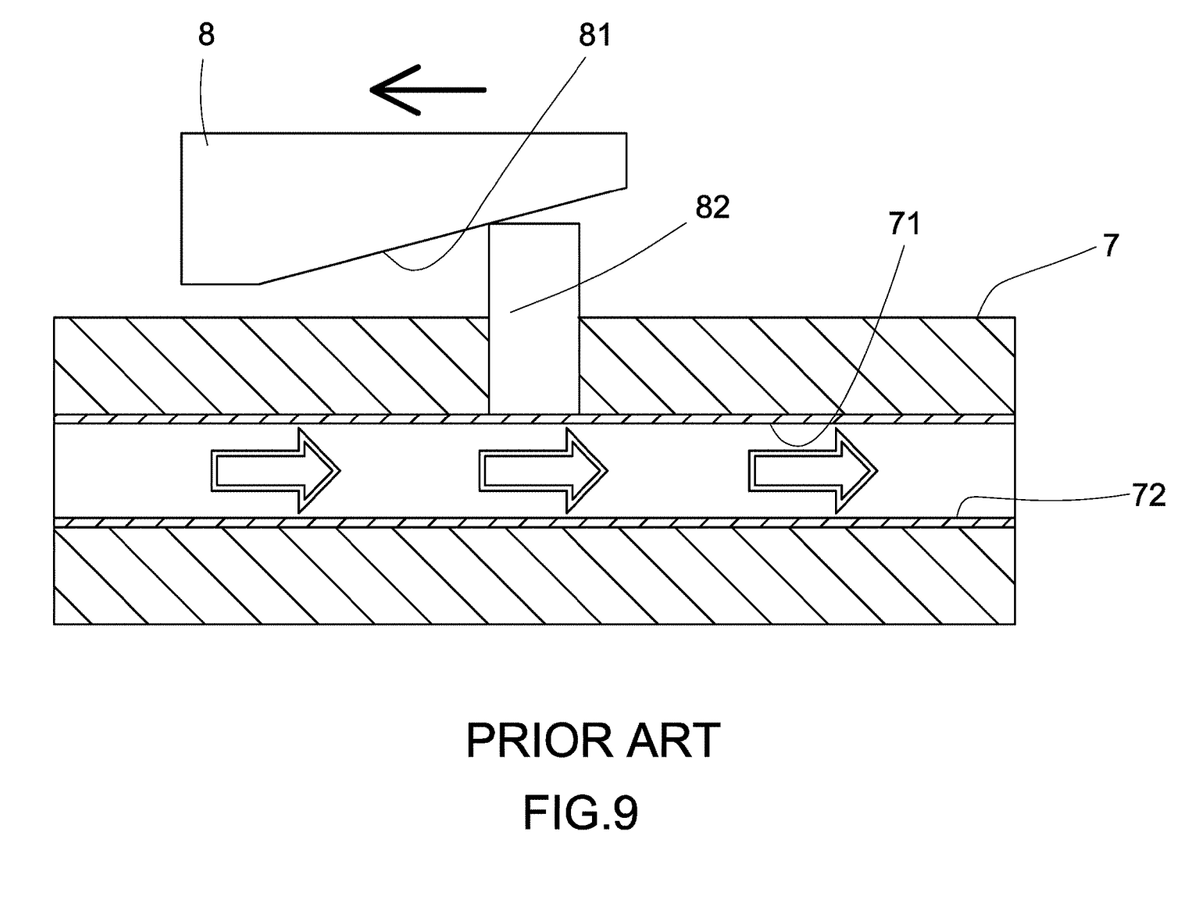
FIG. 9 is a schematic sectional view of a medical catheter control valve according to the prior art.
Figure 10:
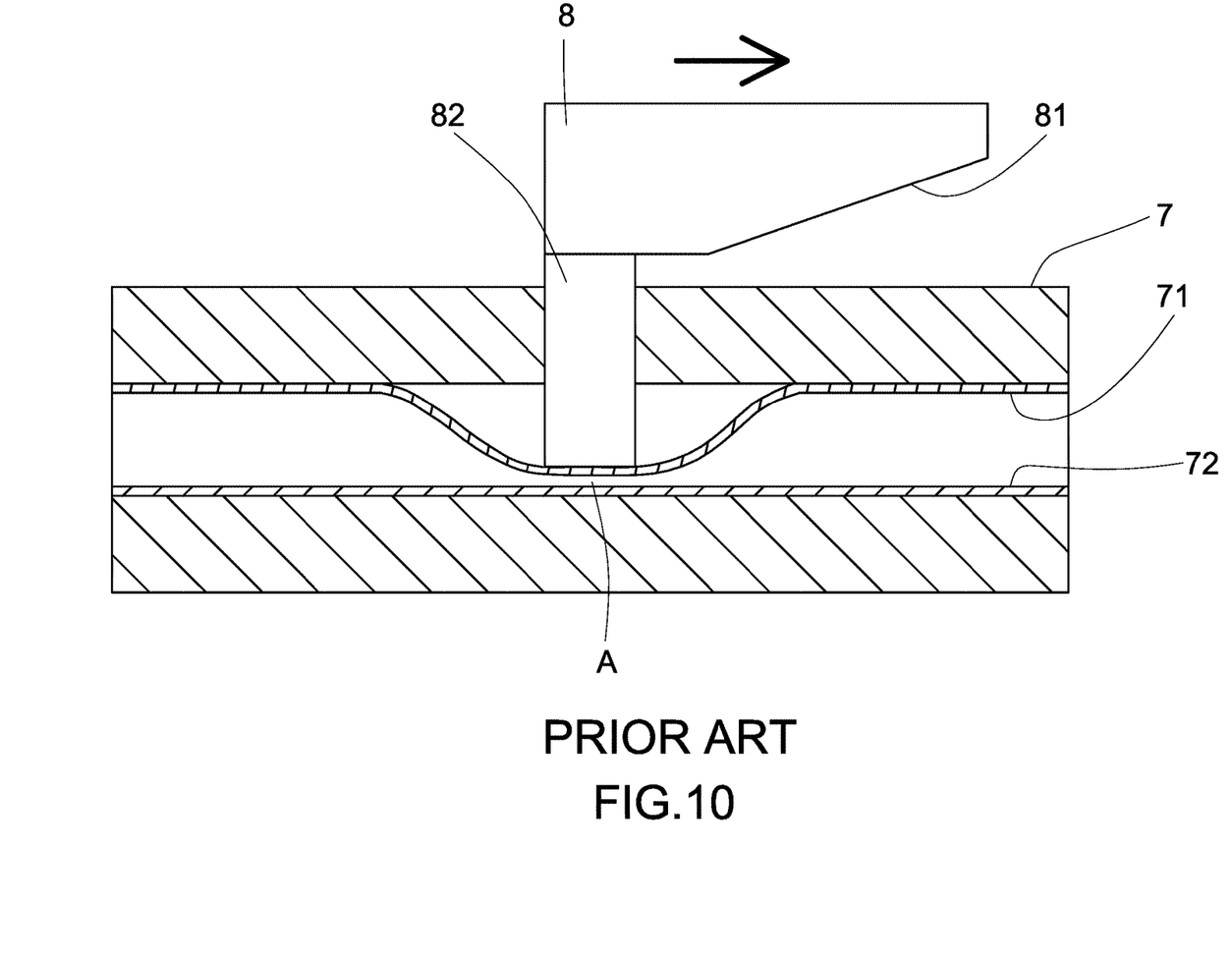
FIG. 10 corresponds to FIG. 9, illustrating the medical catheter control valve closed.

FIGS. 9 and 10 illustrate a medical catheter control valve according to the prior art. As illustrated, the control valve comprises a valve body 7 defining thereof a channel 71, a flexible tube 72 mounted in the channel 71, a pressure rod 82 inserted through a transverse hole (not shown) in the periphery of the valve body 7 and disposed in contact with the periphery of the flexible tube 72, and a sliding control member 8 operable to move the pressure rod 82 transversely relative to the valve body 7. The sliding control member 8 has a beveled edge 81 located on a bottom side thereof and disposed in contact with the pressure rod 82. When pushing the sliding control member 8 forward, the beveled edge 81 is forced to move the pressure rod 82 against the flexible tube 72, thereby deforming the flexible tube 72 to block the passage.

According to the aforesaid prior art design, the flexible tube 72 is mounted in the channel 71 of the valve body 7. When the flexible tube 72 is compressed by the pressure rod 82, the flexible tube 72 will be forced to expand sideways, however, this expanding action will be limited by the inner perimeter of the valve body 7, causing creation of a gap A in the compressed flexible tube 72, thus, the flexible tube 72 cannot be completely blocked, affecting the implementation of the medical operation.

SUMMARY OF THE INVENTION

The present invention has been accomplished under the circumstances in view. It is the main object of the present invention to provide a medical catheter control valve, which uses a click-on mechanism for operation control, allowing the user to close or open the fluid channel with one single hand.

It is the main object of the present invention to provide a medical catheter control valve, which allows operation using one single hand and, can be accurately and rapidly controlled to close or open the fluid channel.

To achieve these and other objects of the present invention, a medical catheter control valve comprises a valve body) and a click-on mechanism. The valve body comprises a fluid channel longitudinally extended through opposing top and bottom ends thereof, and a single open-end hole transversely extended across the fluid channel. The click-on mechanism is mounted in the single open-end hole of the valve body and extending across the fluid channel, comprising a plunger unit and a spring member. The plunger unit defines therein a through hole. When clicks the plunger unit, the elastic restoring energy of the spring member immediately pushes the plunger unit in direction toward the outside of the single open-end hole of the valve body to a first position where the through hole of the plunger unit is shifted into alignment with the fluid channel of the valve body, allowing a fluid to pass through the fluid channel. When push the plunger unit in the single open-end hole of the valve body into a second position, the through hole of the plunger unit is deviated from the fluid channel of the valve body, at this time, the fluid channel is blocked by the plunger unit. Thus, the medical catheter control valve can be conveniently controlled with one single hand.

Other advantages and features of the present invention will be fully understood by reference to the following specification in junction with the accompanying drawings, in which like reference signs denote like components of structure.

DETAILED DESCRIPTION OF THE PREFERRED EMBODIMENT

Figure 1:
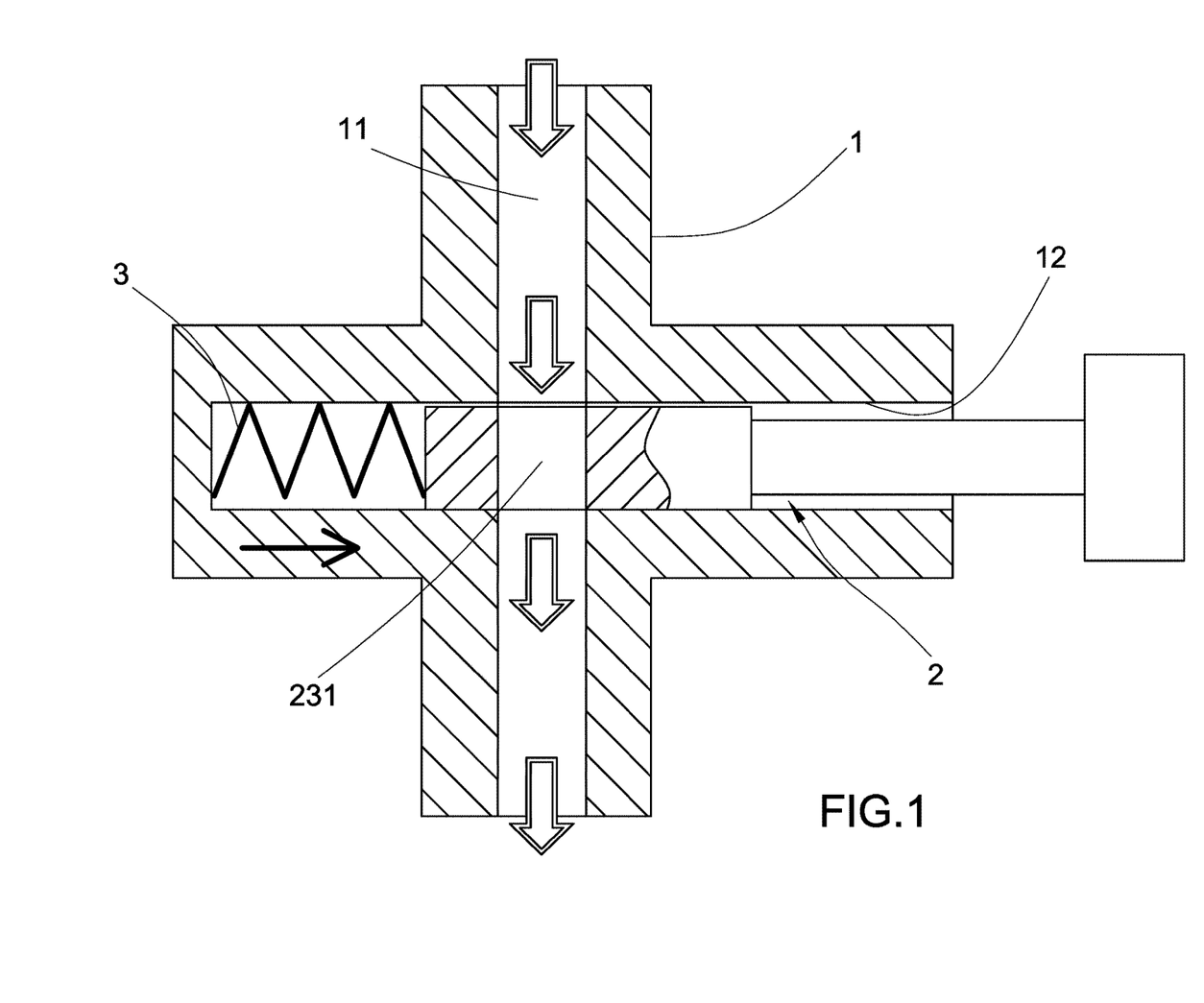
FIG. 1 is a schematic drawing illustrating the architecture of a medical catheter control valve in accordance with the present invention.
Figure 2:
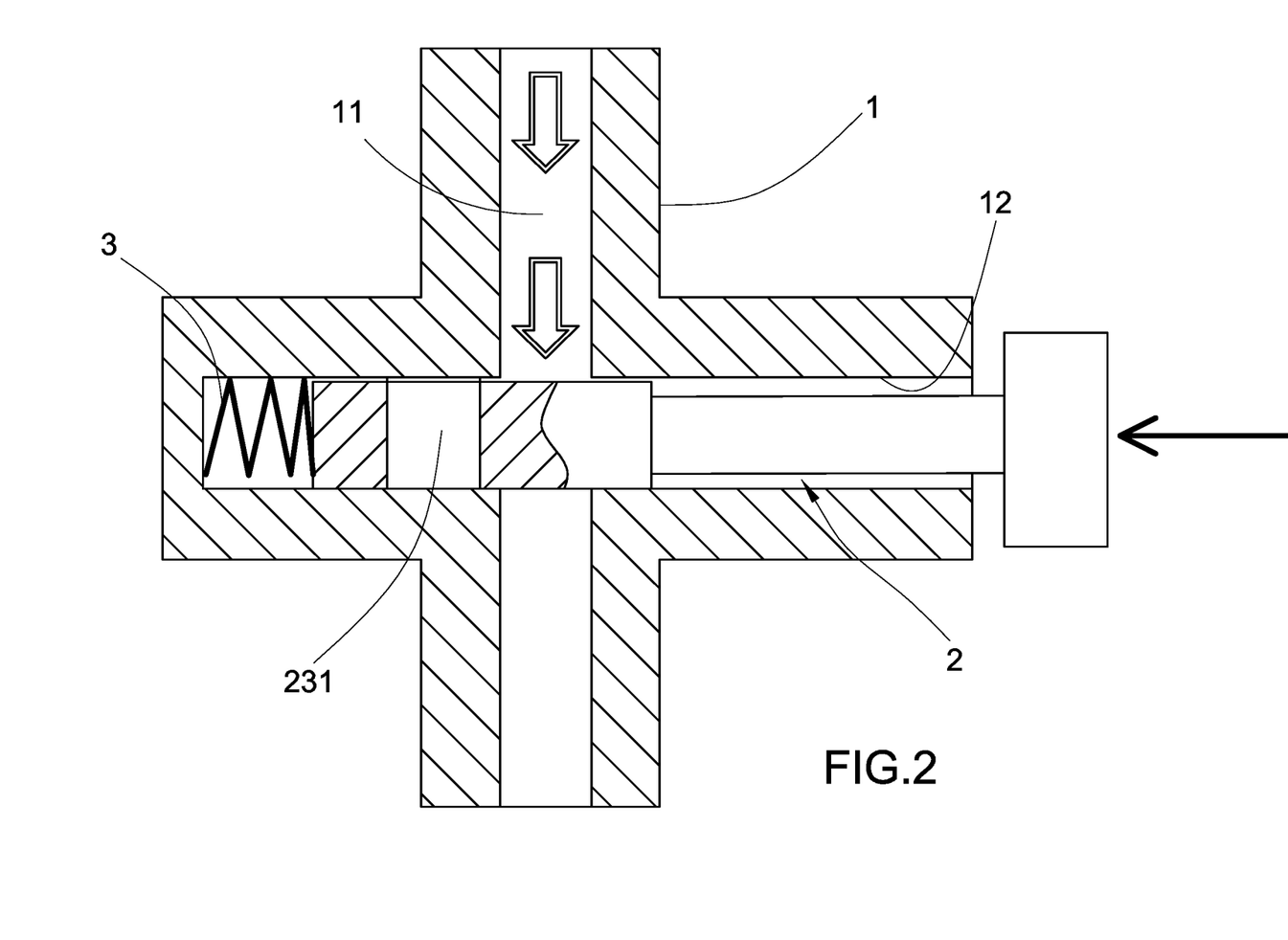
FIG. 2 corresponds to FIG. 1, illustrating the fluid channel of the valve body blocked.

Referring to FIG. 1 and FIG. 2, an architecture of a medical catheter control valve in accordance with the present invention is shown. The medical catheter control valve comprises a valve body 1 and a click-on mechanism 2.

The valve body 1 comprises a fluid channel 11 longitudinally extended through opposing top and bottom ends thereof, and a single open-end hole 12 transversely extended across the fluid channel 11.

The click-on mechanism 2 is mounted in the single open-end hole 12 of the valve body 1 and extending across the fluid channel 11, comprising a plunger unit and a spring member 3. The plunger unit defines therein a through hole 231. When clicks the plunger unit, the elastic restoring energy of the spring member 3 immediately pushes the plunger unit in direction toward the outside of the single open-end hole 12 of the valve body 1 to a first position where the through hole 231 of the plunger unit is shifted into alignment with the fluid channel 11 of the valve body 1, allowing a fluid to pass through the fluid channel 11. When push the plunger unit in the single open-end hole 12 of the valve body 1 into a second position, the through hole 231 of the plunger unit is deviated from the fluid channel 11 of the valve body 1, at this time, the fluid channel 11 is blocked by the plunger unit. Thus, the medical catheter control valve can be conveniently controlled with one single hand.

Figure 3:
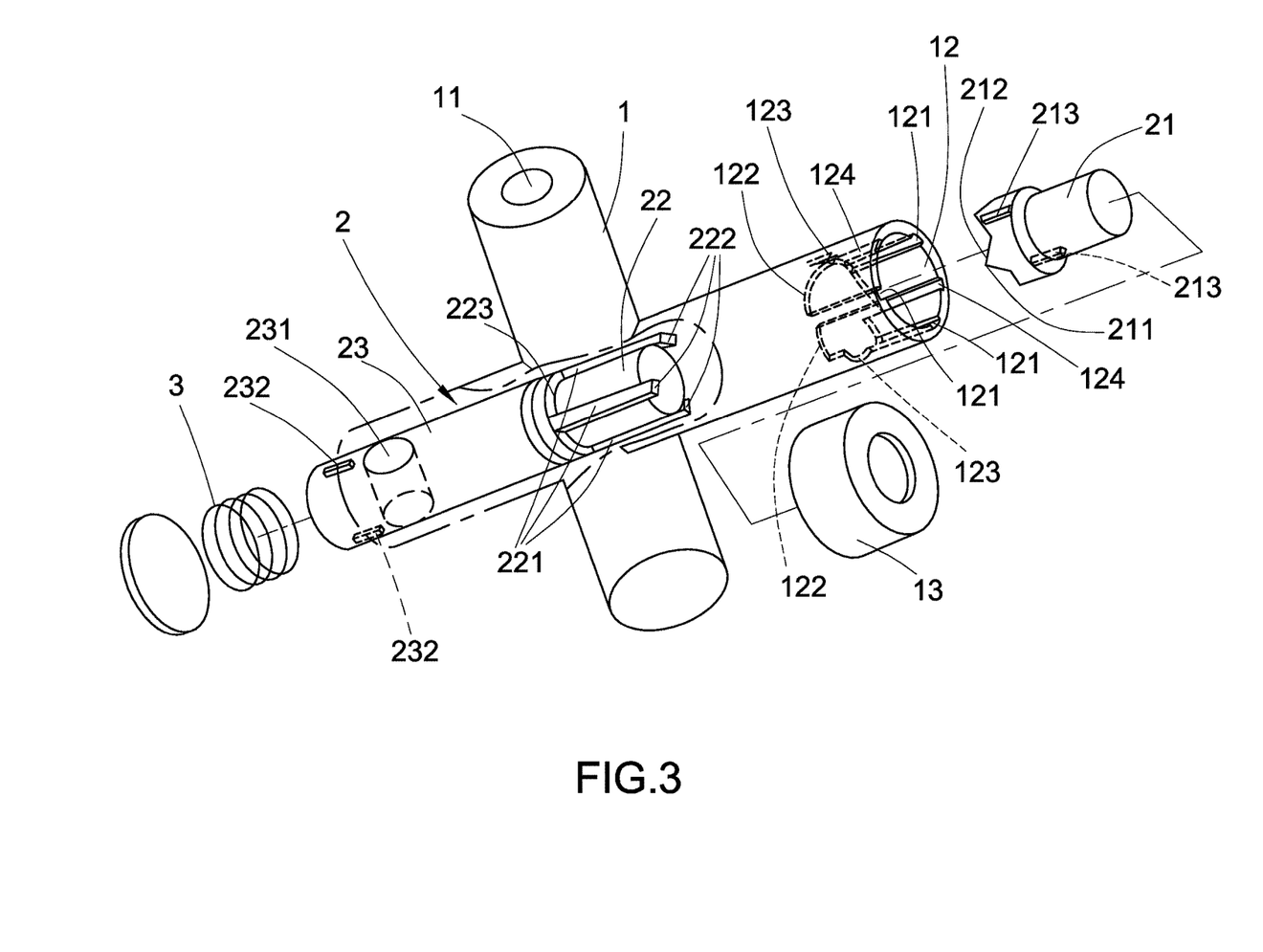
FIG. 3 is an exploded view of the medical catheter control valve in accordance with the first embodiment of the present invention.
Figure 4:
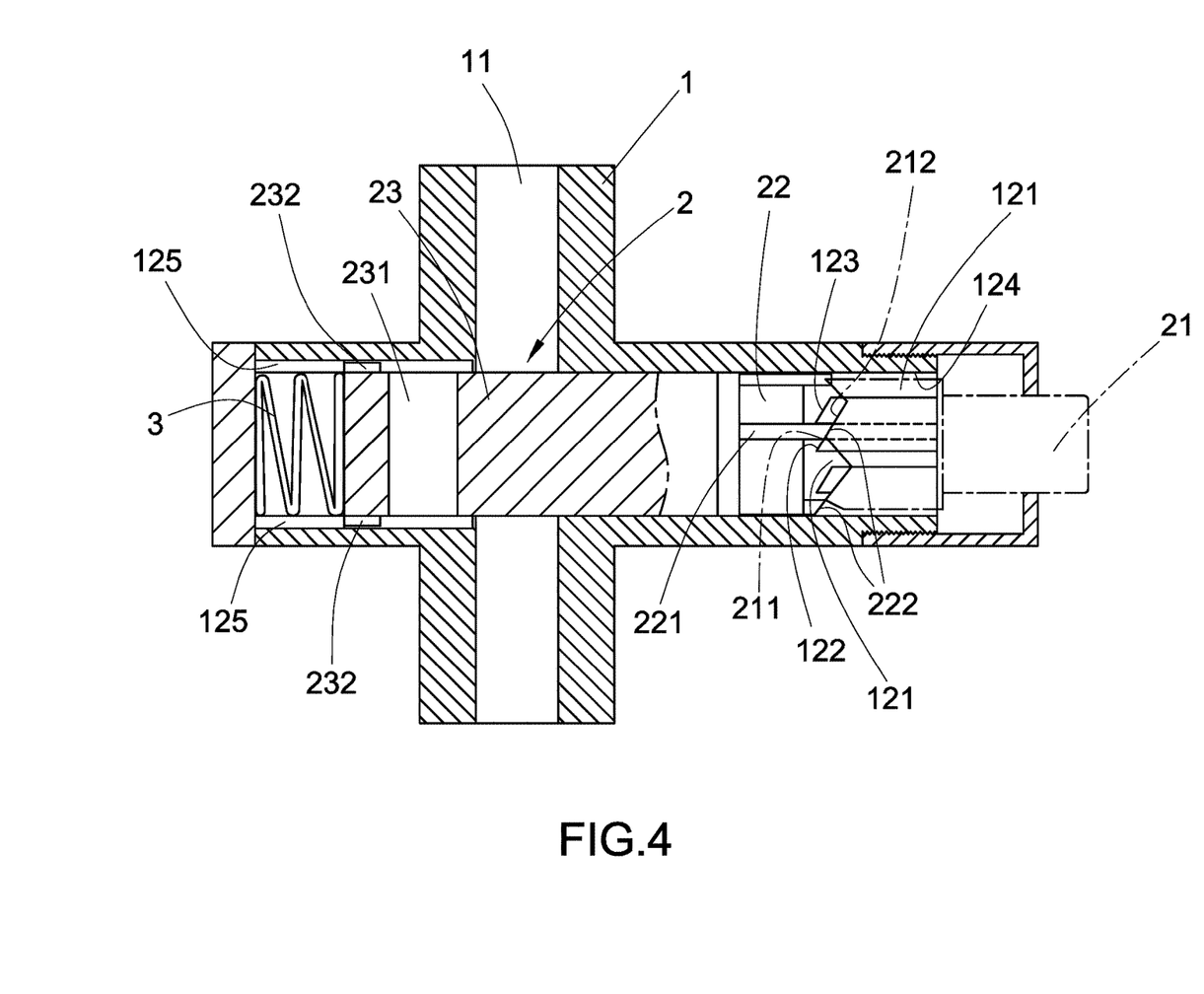
FIG. 4 is a schematic sectional view of the first embodiment of the present invention, illustrating the fluid channel of the valve body blocked.
Figure 5:
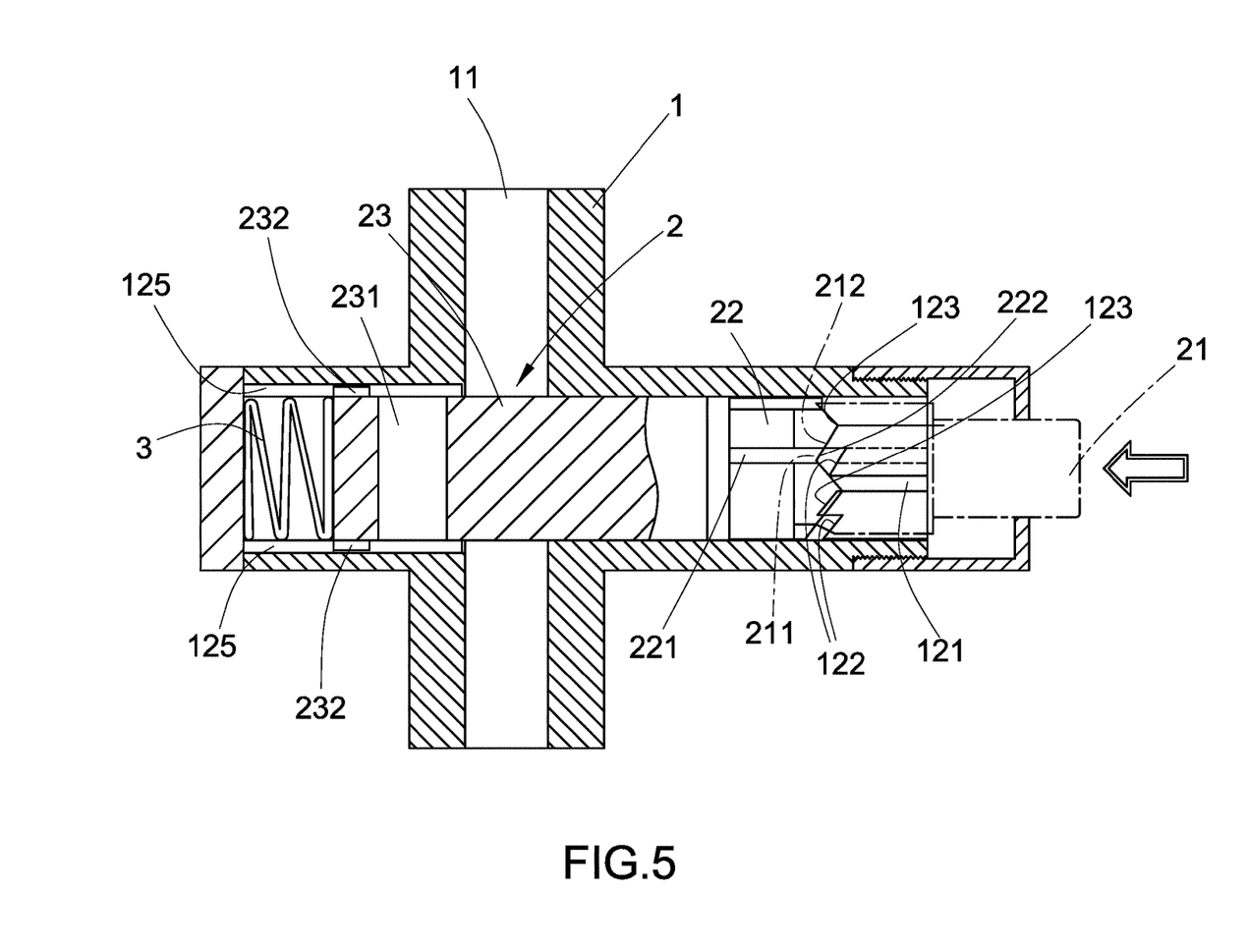
FIG. 5 is a schematic sectional view of the first embodiment of the present invention, illustrating the end piece pushed.
Figure 6:
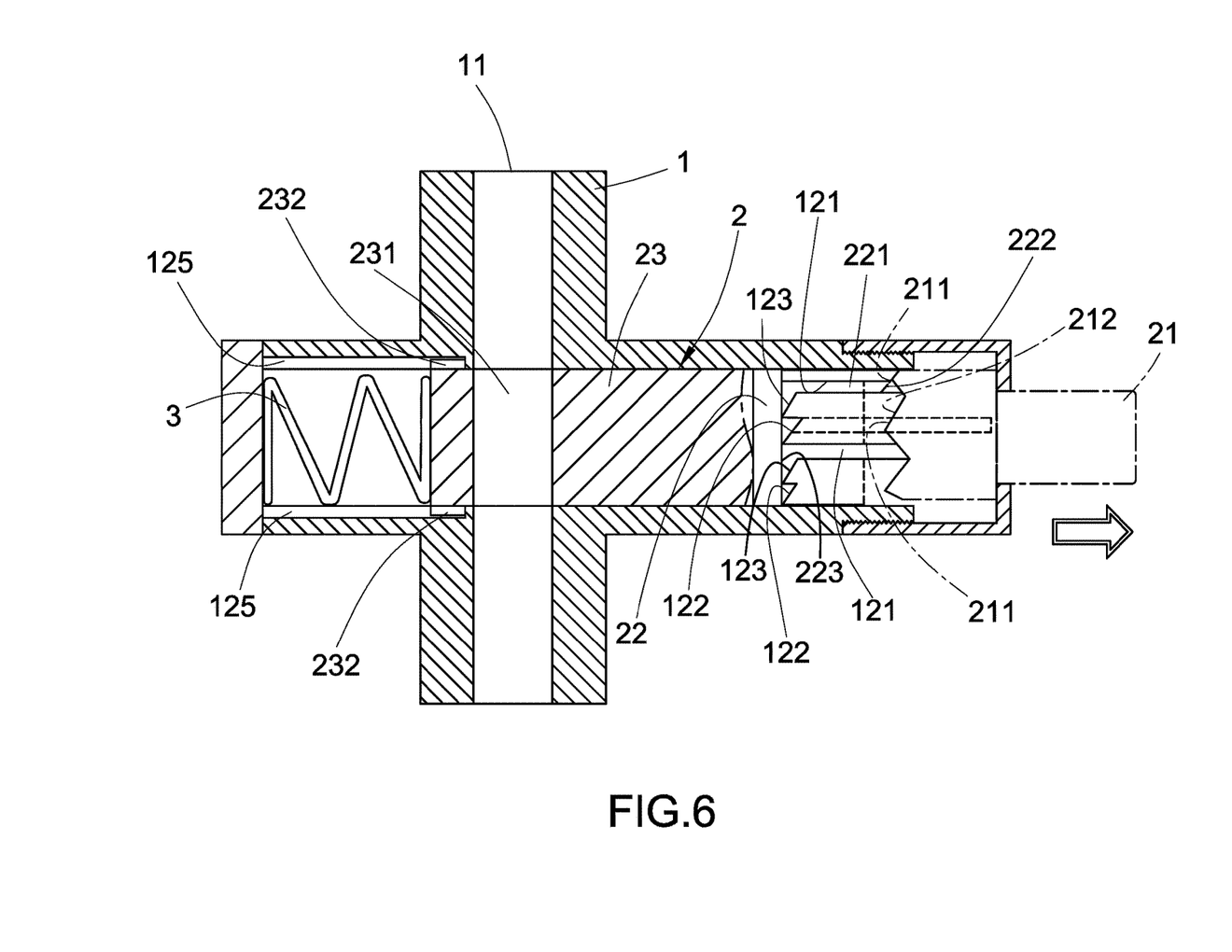
FIG. 6 is schematic sectional view of the first embodiment of the present invention, illustrating the fluid channel of the valve body opened.

Referring to FIG. 3, in a first embodiment of the present invention, the click-on mechanism 2 comprises a plunger unit and a spring member 3. The plunger unit comprises an end piece 21, a positioning control member 22 and a main shaft 23. The end piece 21 comprises a plurality of jagged protrusions 211 equiangularly arranged at one end thereof. Each jagged protrusion 211 has two beveled edges 212 respectively located on two opposite lateral sides thereof. The positioning control member 22 comprises a plurality of rails 221 spaced around one end thereof corresponding to the jagged protrusions 211 of the end piece 21. Each rail 221 has a beveled edge 222. The valve body 1 further comprises a plurality of sliding grooves 121 spaced around an inner peripheral wall of the single open-end hole 12 for the sliding of the respective rails 221 of the positioning control member 22, a first beveled edge 122 and a second beveled edge 123 located on the inner peripheral wall of the single open-end hole 12 and connected between each two adjacent sliding grooves 121. The main shaft 23 is normally forced by the spring member 3 to move the positioning control member 22 into abutment against the end piece 21, keeping the beveled edges 222 of the rails 221 of the positioning control member 22 in contact with respective beveled edges 212 of the jagged protrusions 211 of the end piece 21. When the user pushes the end piece 21 to move the positioning control member 22 and the main shaft 23 toward the inner end of the single open-end hole 12 of the valve body 1 against the spring member 3, the rails 221 of the positioning control member 22 can be moved out of the respective sliding grooves 121 in the single open-end hole 12 of the valve body 1, at this time, subject to the elastic restoring force of the spring member 3, the beveled edges 222 of the rails 221 of the positioning control member 22 will slide along the respective beveled edges 212 of the jagged protrusions 211 of the end piece 21, causing rotation of the positioning control member 22 to the extent that the beveled edges 222 of the rails 221 are positioned in the junctions between the respective first beveled edges 122 and the respective second beveled edges 123. When the beveled edges 222 of the rails 221 are positioned in the junctions between the respective first beveled edges 122 and the respective second beveled edges 123, the through hole 231 of the main shaft 23 is deviated from the fluid channel 11 of the valve body 1, and thus, the fluid channel 11 is blocked (see FIG. 4). When the user presses the end piece 21 again to push the positioning control member 22 and the main shaft 23, the beveled edges 222 of the rails 221 of the positioning control member 22 can be shifted to the respective second beveled edges 123 (see FIG. 5), at this time, the beveled edges 222 of the rails 221 can be moved along the respective beveled edges 212 of the jagged protrusions 211 of the end piece 21, causing rotation of the positioning control member 22. Thus, when the beveled edges 222 of the rails 221 are moved along the respective second beveled edges 123, the positioning control member 22 is rotated, enabling the rails 221 to be moved into the respective sliding grooves 121 in the single open-end hole 12 of the valve body 1, so that the main shaft 23 and the positioning control member 22 can be synchronously moved to the right side (outer side) and stopped in the position where the first and second beveled edges 122,123 are stopped at respective stop edges 223 near the bottom side of the positioning control member 22. At this time, the through hole 231 of the main shaft 23 is kept in alignment with the fluid channel 11 of the valve body 1, and thus, the fluid channel 11 is opened for the passing of a fluid (see FIG. 6). Further, the main shaft 23 and end piece 21 have longitudinal ribs 232,213 arranged around the periphery thereof for slidably coupled to sliding grooves 125,124 in the single open-end hole 12 of the valve body 1 to prevent rotation of the main shaft 23 and the end piece 21 relative to the valve body 1. Further, an end cap 13 is capped on the valve body 1 to hold the end piece 21 in place, preventing the end piece 21 from falling out of the single open-end hole 12.

Figure 7:
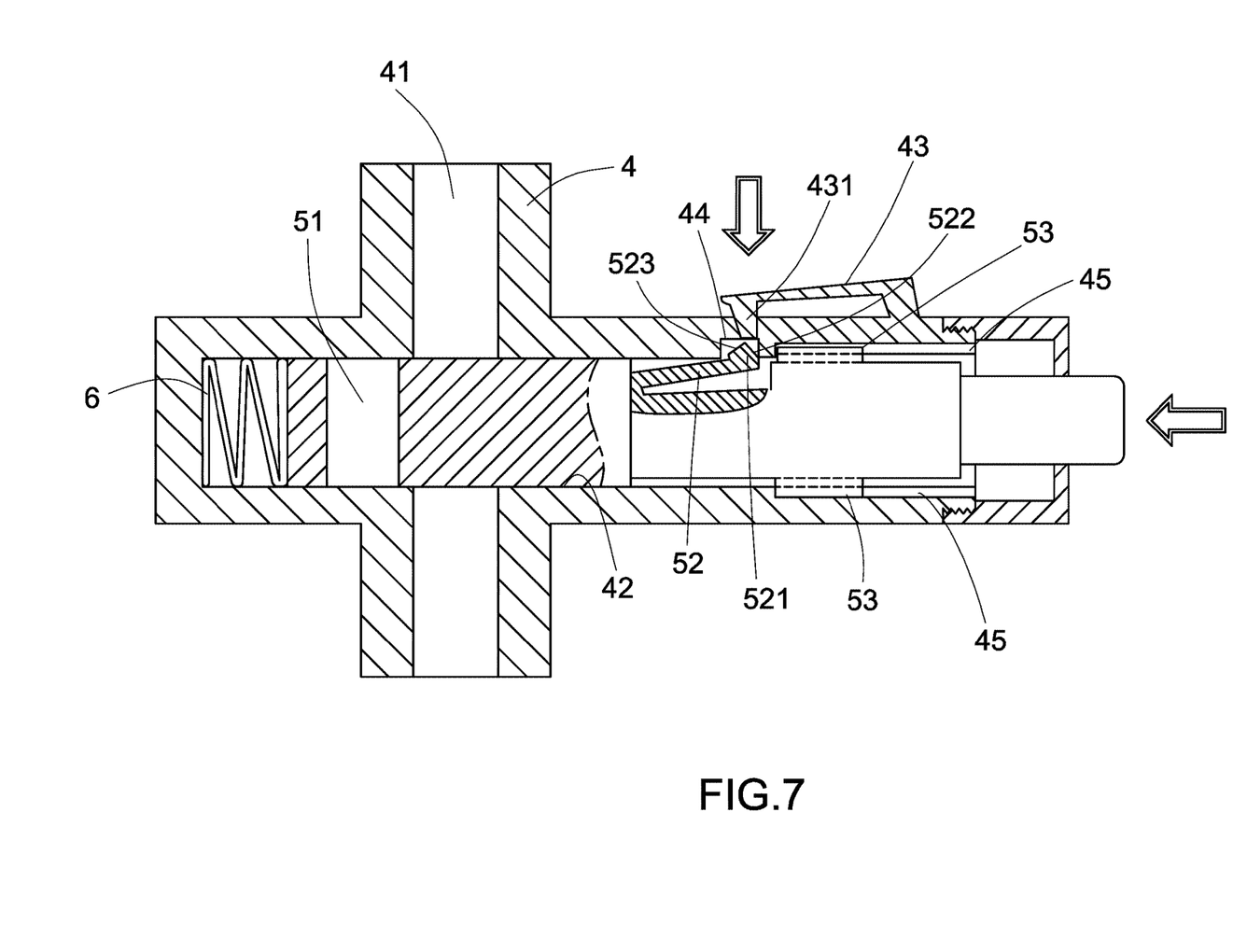
FIG. 7 is a schematic sectional view of a medical catheter control valve in accordance with a second embodiment of the present invention.
Figure 8:
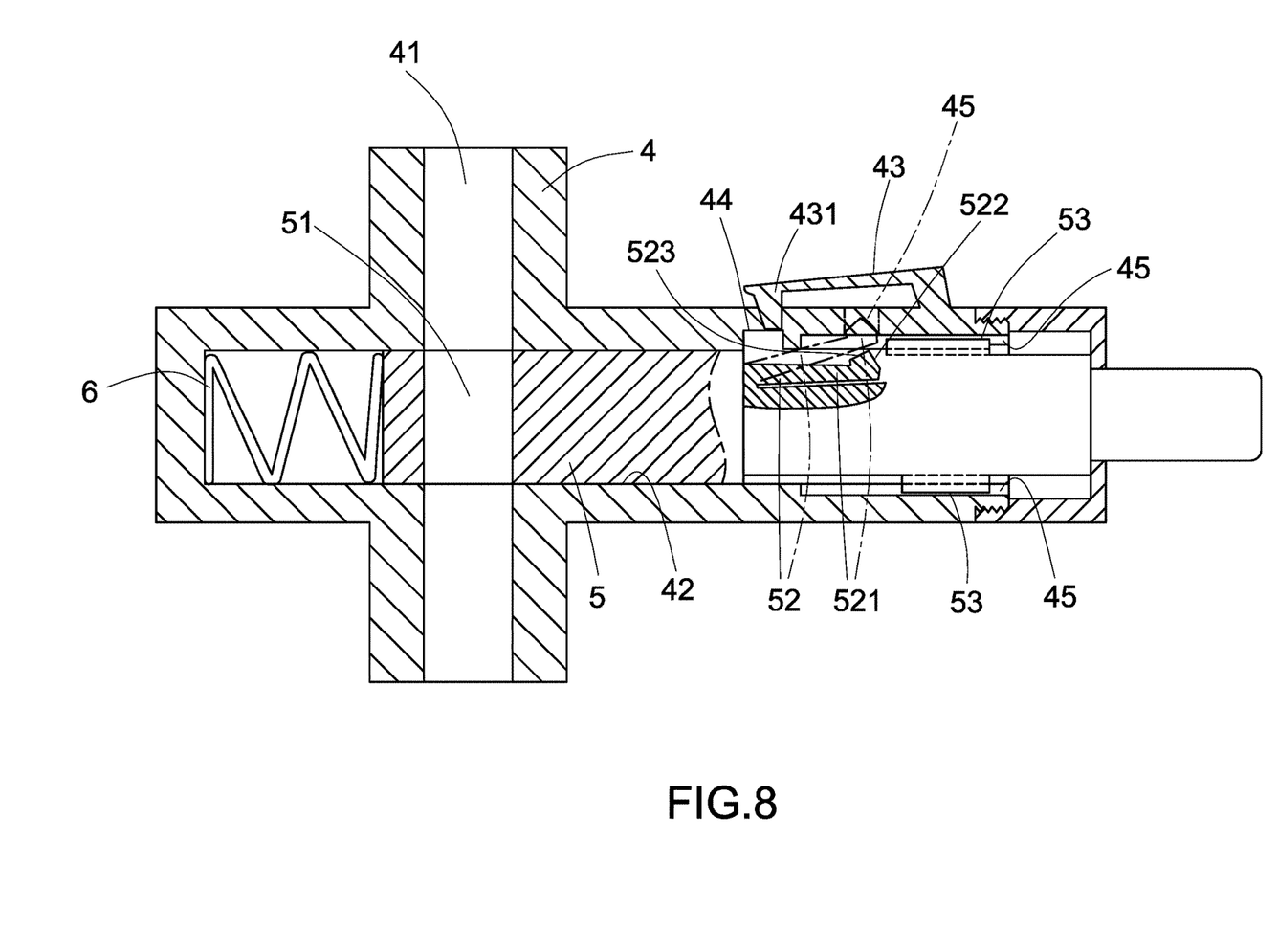
FIG. 8 corresponds to FIG. 7, illustrating the fluid channel of the valve body opened.

Referring to FIGS. 7 and 8, a medical catheter control valve in accordance with a second embodiment of the present invention is shown. The medical catheter control valve comprises a valve body 4 and a click-on mechanism.

The valve body 4 comprises a fluid channel 41 longitudinally extended through opposing top and bottom ends thereof, and a single open-end hole 42 transversely extended across the fluid channel 41.

The click-on mechanism is mounted in the single open-end hole 42 of the valve body 4 and extending across the fluid channel 41, comprising a plunger 5 and a spring member 6. The plunger 5 comprises an elastic positioning member 52 terminating in an engagement tip 521. The engagement tip 521 defines an engagement edge 522 at one side thereof and a beveled edge 523 at an opposite side thereof. The valve body 4 comprises a retaining hole 44 cut through the periphery thereof in communication with the single open-end hole 42 for securing the engagement tip 521 of the elastic positioning member 52 of the plunger 5, a springy release control member 43 extended from the periphery thereof and terminating in a pushing portion 431 that faces toward the retaining hole 44. When the user pushes the plunger 5 toward the inside of the single open-end hole 42, the engagement tip 521 of the elastic positioning member 52 is forced into the retaining hole 44 of the valve body 4 to hold the plunger 5 in a position where the through hole 51 of the plunger 5 is deviated from the fluid channel 41 of the valve body 4 and the fluid channel 41 is blocked by the plunger 5. When the user presses the springy release control member 43 of the valve body 4 to force the pushing portion 431 into the retaining hole 44, the engagement tip 521 of the elastic positioning member 52 of the plunger 5 is disengaged from the retaining hole 44, and the plunger 5 is pushed back to its previous position by the spring member 6, keeping the through hole 51 in alignment with the fluid channel 41 of the valve body 4 for allowing a fluid to pass through the fluid channel 41.

Further, the plunger 5 is configured to provide at least one longitudinal rib 53 on the periphery thereof. The at least one longitudinal rib 53 is slidably coupled to respective at least one sliding grooves 46 in the single open-end hole 42 of the valve body 4 to prohibit rotation of the plunger 5 relative to the valve body 4. Further, an end cap 47 is capped on the valve body 4 to prohibit the plunger 5 from falling out of the end piece single open-end hole 42 of the valve body 4. Further, the valve body 4 can be configured to provide a second retaining hole 45. When the user presses the springy release control member 43 of the valve body 4 to force the pushing portion 431 into the retaining hole 44 and to further disengage the engagement tip 521 of the elastic positioning member 52 of the plunger 5 from the retaining hole 44, the plunger 5 will be pushed back by the spring member 6. At this time, the engagement tip 521 of the elastic positioning member 52 will be forced into the second retaining hole 45, holding the plunger 5 in the open position where the through hole 51 is kept in alignment with the fluid channel 41 of the valve body 4 for allowing a fluid to pass through the fluid channel 41.

In conclusion, the medical catheter control valve allows operation with one single hand to open or close the fluid channel rapidly and conveniently.

What the invention claimed is:

1. A medical catheter control valve, comprising:

a valve body comprising a fluid channel longitudinally extending through opposing top and bottom ends thereof, and a single open-end hole transversely extended across said fluid channel; and a click-on mechanism mounted in said single open-end hole of said valve body, said click-on mechanism including a plunger unit and a spring member, said plunger unit including a through hole, said plunger unit and said spring member being configured that when said plunger unit is sequentially depressed and released, said spring member exerts a bias force to push said plunger unit to a first position in said single open-end hole of said valve body where said through hole of said plunger unit is disposed in alignment with said fluid channel of said valve body for allowing a fluid to pass through said fluid channel; when said plunger unit is again sequentially depressed and released, said plunger unit is thereby positioned in a second position where said through hole of said plunger unit is displaced from alignment with said fluid channel of said valve body and said fluid channel is thereby blocked by said plunger unit to prohibit flowing of a fluid therethrough, said plunger unit of said click-on mechanism further including an end piece, a positioning control member and a main shaft, said end piece comprising a plurality of jagged protrusions equiangularly arranged on one end thereof, said positioning control member comprising a plurality of rails equiangularly arranged around one end thereof and facing toward the respective said jagged protrusions of said end piece, each said rail having a beveled edge on a distal end thereon; said valve body further comprises a plurality of sliding grooves equiangularly spaced around an inner peripheral wall of said single open-end hole for allowing the respective said rails of said positioning control member to slide therein, a first beveled edge and a second beveled edge located on said inner peripheral wall of said single open-end hole between each two adjacent said sliding grooves and connected in series, said main shaft being normally forced by said spring member to move said positioning control member into abutment against said end piece to keep said beveled edges of said rails of said positioning control member in contact with respective said beveled edges of said jagged protrusions of said end piece so that when a user pushes said end piece to move said positioning control member and said main shaft toward the inside of said single open-end hole of said valve body against said spring member, said rails of said positioning control member are moved out of the respective said sliding grooves in said single open-end hole of said valve body, at this time, subject to the elastic restoring force of said spring member, said beveled edges of said rails of said positioning control member are forced to slide along the respective said beveled edges of said jagged protrusions of said end piece, causing rotation of said positioning control member to the extent that said beveled edges of said rails are positioned in respective junctions between the respective said first beveled edges and the respective said second beveled edges and said through hole of said main shaft is deviated from said fluid channel of said valve body, and thus, said fluid channel is blocked by said plunger unit; when the user presses said end piece again to push said positioning control member and said main shaft, said beveled edges of said rails of said positioning control member are shifted to the respective said second beveled edges, at this time, said beveled edges of said rails are moved along the respective said beveled edges of said jagged protrusions of said end piece, causing rotation of said positioning control member and enabling said rails to be moved into the respective said sliding grooves in said single open-end hole of said valve body, and thus, said main shaft and said positioning control member are synchronously moved into said first position where said first and second beveled edges are stopped at respective stop edges near a bottom side of said positioning control member and said through hole of said plunger unit is disposed in alignment with said fluid channel of said valve body for allowing a fluid to pass through said fluid channel.

2. The medical catheter control valve as claimed in claim 1, wherein said main shaft comprises at least one longitudinal rib; said valve body further comprises at least one sliding groove located in said single open-end hole for receiving said at least one longitudinal rib of said main shaft to prohibit said main shaft from rotation relative to said valve body.

3. The medical catheter control valve as claimed in claim 1, wherein said end piece comprises at least one longitudinal rib; said valve body further comprises at least one sliding groove located in said single open-end hole for receiving said at least one longitudinal rib of said end piece to prohibit said end piece from rotation relative to said valve body.

4. The medical catheter control valve as claimed in claim 1, further comprising an end cap capped on said valve body to hold said end piece in said single open-end hole in place and to stop said end piece from falling out of said single open-end hole.

5. A medical catheter control valve, comprising:

a valve body comprising a fluid channel longitudinally extending through opposing top and bottom ends thereof, a single open-end hole transversely extended across said fluid channel, a retaining hole cut through a periphery thereof in communication with said single open-end hole, and a springy release control member extended from the periphery thereof and pressable to insert into said retaining hole; and a click-on mechanism comprising a spring member mounted in said single open-end hole of said valve body and a plunger slidably inserted into said single open-end hole of said valve body and stopped against said spring member, said plunger comprising an elastic positioning member extended from the periphery thereof and terminating in an engagement tip and a through hole transversely cut through the periphery thereof;

wherein said plunger is movable by an external force toward the inside of said single open-end hole against said spring member to force said elastic positioning member of said engagement tip into said retaining hole of said valve body so that said plunger is held in a close position where said through hole of said plunger is deviated from said fluid channel of said valve body and said fluid channel is blocked by said plunger, said springy release control member of said valve body is pressable by an external force to force a pushing portion into said retaining hole, moving said engagement tip of said elastic positioning member of said plunger out of said retaining hole and enabling said plunger to be pushed back by said spring member to an open position where said through hole is kept in alignment with said fluid channel of said valve body for allowing a fluid to pass through said fluid channel.

6. The medical catheter control valve as claimed in claim 5, wherein said engagement tip of said elastic positioning member defines an engagement edge on one side thereof and a beveled edge on an opposite side thereof.

7. The medical catheter control valve as claimed in claim 5, wherein said plunger comprises at least one longitudinal rib located on the periphery thereof; said valve body further comprises at least one sliding groove disposed in said single open-end hole for receiving said at least one longitudinal rib of said plunger to prohibit rotation of said plunger relative to said valve body.

8. The medical catheter control valve as claimed in claim 5, wherein said valve body further comprises a second retaining hole for securing said engagement tip of said elastic positioning member to hold said plunger in said open position.

* * * * *